United States Patent [19]

Kis-Tamás et al.

[11] Patent Number: 4,469,703

[45] Date of Patent: Sep. 4, 1984

[54] NITROALKANOL DERIVATIVES AND PLANT PROTECTING AGENTS CONTAINING THE SAME

[75] Inventors: Attila Kis-Tamás; Gyula Mikite, both of Budapest; Erzsébet Csuták née Jakucs, Budaörs; László Kocsis, Budapest, all of Hungary

[73] Assignee: Egyt Gyogyszervegyeszeti Gyar, Budapest, Hungary

[21] Appl. No.: 350,570

[22] Filed: Feb. 22, 1982

Related U.S. Application Data

[63] Continuation of Ser. No. 174,262, Jul. 31, 1980, abandoned.

[30] Foreign Application Priority Data

Jul. 26, 1979 [HU] Hungary ................. EE 2684

[51] Int. Cl.³ .................. A01N 37/02; A01N 43/16; A01N 37/06; C07C 67/02
[52] U.S. Cl. .................................. 424/311; 549/444; 549/491; 560/110; 560/261; 560/254; 560/262; 560/264; 424/282
[58] Field of Search ............... 560/110, 261, 254, 264; 424/311, 282; 549/444

[56] References Cited

U.S. PATENT DOCUMENTS

| | | | |
|---|---|---|---|
| 2,185,297 | 1/1940 | Gloor | 560/264 |
| 2,340,268 | 1/1944 | Hass et al. | 560/264 |
| 2,402,776 | 6/1946 | Robinette | 560/264 |
| 2,967,829 | 1/1961 | Bennett | 560/264 |
| 2,976,244 | 3/1961 | Bennett | 560/110 |
| 3,149,031 | 9/1964 | Stoffel et al. | 560/110 |
| 3,723,546 | 3/1973 | Bachman et al. | 560/264 |
| 3,931,412 | 1/1976 | Kensler, Jr. et al. | 560/264 |
| 4,160,035 | 7/1979 | Levai et al. | 560/254 |
| 4,219,660 | 8/1980 | Wehrli et al. | 560/253 |

OTHER PUBLICATIONS

Chem. Abstracts, 63:14750g, (1964).

Primary Examiner—Ethel G. Love

Attorney, Agent, or Firm—Young & Thompson

[57] ABSTRACT

The invention relates to nitroalkanol derivatives of the general formula (I),

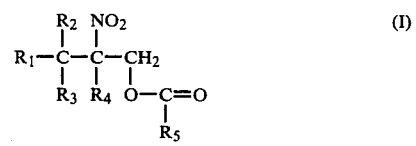

wherein
  $R_1$ is a $C_{2-12}$ alkenyl or alkadienyl group, a $C_{4-12}$ alkoxyalkyl or alkoxyalkenyl group having one or more $C_{1-3}$ alkyl substituents, a $C_{3-6}$ cycloalkyl or cycloalkenyl group, a furyl group, a nitrofuryl group, or a phenyl group having optionally one or more identical or different substituents selected from the group consisting of hydroxy, $C_{1-4}$ alkoxy, halogen, nitro, $C_{1-4}$ alkylenedioxy and $C_{1-4}$ alkenoyloxy groups,
  $R_2$ and $R_4$ each represent hydrogen or they form together a valence bond,
  $R_3$ is a $C_{1-12}$ alkanoyloxy group, a benzoyloxy group having optionally one or more halogen substituents or hydrogen atom, and
  $R_5$ is a $C_{1-12}$ alkyl group or a phenyl group having optionally one or more halogen substituents,
with the proviso that if $R_2$ and $R_4$ each stand for hydrogen, $R_1$ is other than unsubstituted phenyl and $R_3$ may represent only a $C_{1-4}$ alkanoyloxy group or a benzoyloxy group having optionally one or more halogen substituents, and with the further proviso that if $R_2$ and $R_4$ form together a valence bond and $R_5$ is methyl, $R_1$ is other than unsubstituted phenyl.

The nitroalkenol derivatives defined above as well as the known 1-phenyl-2-nitro-3-acetoxy-propane-1 possess valuable pesticidal effects, primarily fungicidal activities, and can be applied to advantage in the agriculture as plant protecting agents.

5 Claims, No Drawings

NITROALKANOL DERIVATIVES AND PLANT PROTECTING AGENTS CONTAINING THE SAME

This application is a continuation, of application Ser. No. 174,262, filed July 31, 1980, now abandoned.

The invention relates to new nitroalkanol derivatives and plant protecting agents which contain the new compounds.

It is known that certain nitroalkanol derivatives are effective against humanpathogeneous pests and exert anthelminthic activity (British patent Specification No. 1,449,540). 1-Phenyl-2-nitro-3-acetoxy-propen-1 has already been described in the literature, no reference is given, however, about its biological properties, and the known method of the preparation of this compound also differs from the methods of the invention.

In one aspect, the present invention relates to new compounds of the general formula (I),

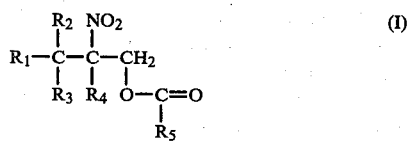

wherein
$R_1$ is a $C_{2-12}$ alkenyl or alkadienyl group, a $C_{4-12}$ alkoxyalkyl or alkoxyalkenyl group having one or more $C_{1-3}$ alkyl substituents, a $C_{3-6}$ cycloalkyl or cycloalkenyl group, a furyl group, a nitrofuryl group, or a phenyl group having optionally one or more identical or different substituents selected from the group consisting of hydroxy, $C_{1-4}$ alkoxy, halogen, nitro, $C_{1-4}$ alkylenedioxy and $C_{1-4}$ alkanoyloxy groups, $R_2$ and $R_4$ each represent hydrogen or they form together a valence bond, $R_3$ is a $C_{1-12}$ alkanoyloxy group or hydrogen atom, and $R_5$ is a $C_{1-12}$ alkyl group, with the proviso that if $R_2$ and $R_4$ each stand for hydrogen, $R_1$ is other than unsubstituted phenyl and $R_3$ may represent only a $C_{1-4}$ alkanoyloxy group, and with the further proviso that if $R_2$ and $R_4$ form together a valence bond and $R_5$ is methyl, $R_1$ is other than unsubstituted phenyl. The term "$C_{2-12}$ alkenyl or alkadienyl group" refers to straight-chained or branched aliphatic hydrocarbyl groups which contain one or two double bonds, such as propenyl, allyl, buta-1,3-dienyl, 2,6-dimethyl-hept-1-enyl, etc. The alkoxy groups may be of straight and branched chain, such as methoxy, ethoxy, n-propoxy, n-butoxy, isobutoxy, etc. Of the $C_{3-6}$ cycloalkyl groups e.g. the cyclopropyl, cyclobutyl, cyclopentyl and cyclohexyl groups are to be mentioned. The cycloalkenyl groups also contain 3 to 6 carbon atoms, such as cyclopentenyl, cyclohexenyl, etc. If $R_1$ represents phenyl group, it may bear one or more identical or different substituents, such as halogen atoms (fluorine, chlorine, bromine or iodine), hydroxy group, $C_{1-4}$ alkoxy groups, nitro group, $C_{1-4}$ alkanoyloxy groups and/or $C_{1-4}$ alkylenedioxy groups. Of the substituted phenyl groups represented by $R_1$ e.g. the 3-methoxy, 4-methoxy-, 3,4-dimethoxy-, 3,4,5-trimethoxy-, 3,4-methylenedioxy-, 3-nitro-, 4-nitro-, 4-chloro-, 4-bromo-, 4-fluoro-, 3-chloro-, 3-fluoro-, 3-acetoxy-, 4-acetoxy- and 3-methoxy-4-acetoxyphenyl groups are to be mentioned. The term "$C_{1-4}$ alkanoyloxy group" refers to straight-chained and branched alkanoyloxy groups, such as acetoxy, propionyloxy, butyryloxy, etc.

$R_1$ represents preferably a $C_{3-10}$ alkenyl group, a cyclopentyl group, a cyclohexyl group, a furyl group, or a phenyl group having optionally one or more identical or different substituents selected from the group consisting of $C_{1-4}$ alkoxy, halogen, methylenedioxy, nitro and $C_{1-4}$ alkanoyloxy.

$R_3$ is preferably hydrogen atom or acetoxy group, whereas $R_5$ represents preferably a methyl or ethyl group.

Preferred representatives of the compounds having the general formula (I) are those wherein $R_1$ represents a phenyl group having optionally one, two or three $C_{1-2}$ alkyl substituent(s), a methylenedioxy substituent, a nitro substituent or a halogen substituent, or $R_1$ stands for cyclohexyl group or 2-furyl group, $R_2$ and $R_4$ each represent hydrogen or they form together a valence bond, $R_3$ is hydrogen or acetoxy and $R_5$ is methyl.

Particularly preferred representatives of the compounds having the general formula (I) are the following derivatives: 1-(4-nitrophenyl)-2-nitro-1,3-diacetoxypropane, 1-cyclohexyl-2-nitro-1,3-diacetoxypropane, 1-(4-methoxyphenyl)-2-nitro-3-acetoxy-propene-1, 1-(3,4-methylenedioxyphenyl)-2-nitro-3-acetoxy-propene-1, 1-(3-fluorophenyl)-2-nitro-1,3-diacetoxy-propane, 1,3-diacetoxy-2-nitro-4-hexene and 1-(2-furyl)-2-nitro-3-acetoxy-propene-1.

1-Phenyl-2-nitro-3-acetoxy-propene-1 possesses particularly advantageous biological properties.

The compounds of the general formula (I) in which $R_2$ and $R_4$ stand for hydrogen have two centres of asymmetry in positions 1 and 2, consequently they exist in the form of four isomers. The scope of the invention embraces all the possible isomers and isomeric mixtures of the compounds having the general formula (I), as well as the preparation thereof and plant protecting agents which contain such isomers or isomeric mixtures as active compounds.

In a further aspect, the invention relates to pesticidal compositions which contain as active agent at least one compound of the general formula (I), wherein $R_1$ is a $C_{2-12}$ alkenyl or alkadienyl group, a $C_{4-12}$ alkoxyalkyl or alkoxyalkenyl group having one or more $C_{1-3}$ alkyl substituents, a $C_{3-6}$ cycloalkyl or cycloalkenyl group, a furyl group, a nitrofuryl group, or a phenyl group having optionally one or more identical or different substituents selected from the group consisting of hydroxy, $C_{1-4}$ alkoxy, halogen, nitro, $C_{1-4}$ alkylenadioxy and $C_{1-4}$ akanoyloxy groups, $R_2$ and $R_4$ each represent hydrogen or they form together a valence bond, $R_3$ is a $C_{1-12}$ alkanoyloxy group or a hydrogen atom, and $R_5$ is a $C_{1-12}$ alkyl group, with the proviso that if $R_2$ and $R_4$ each stand for hydrogen, $R_1$ is other than unsubstituted phenyl and $R_3$ may represent only a $C_{1-4}$ alkanoyloxy group, in an amount of 0.01 to 95%, together with a conventional solid or liquid carrier and optionally one or more further additive, such as a dispersing agent, a surfactant, an agent modifying the duration of the effect, a stickener and/or a stabilizer.

The active agents listed above are new compounds, with the exception of 1-phenyl-2-nitro-3-acetoxy-propene-1 ($R_1$=phenyl, $R_2$ and $R_4$ form together a valence bond, $R_3$ is hydrogen and $R_5$ is acetoxy). This latter compound was described in the literature [C.A. 63, 14750 g (1964); Bull. Chem. Soc. Jap. 38 (8), 1237-40] as an intermediate, without reporting, however, about its possible biological effects.

The invention relates particularly to fungicidal preparations which contain one or more compounds of the general formula (I), wherein the substituents are as defined just above.

The pesticidal compositions according to the invention can be prepared by methods known per se, utilizing conventional carriers and/or auxiliary agents. These compositions may contain, beside the active agent, usual additives, such as solubilizing agents, carriers, diluents, extenders, dispersing agents, surfactants, agents modifying the duration of the effect, stickeners and/or stabilizers.

The active compounds of the general formula (I) may be formulated into usual compositions, such as solutions, emulsions, suspensions, powders, dispersible powders, spray powders, wettable powders, foams, pulps, granulates, aerosols, emulsifiable concentrates, suspension concentrates, compositions for seed dressing, etc. Of these compositions the wettable powders (WP; primarily those containing 50% of active agent), emulsifyable concentrates (EC), colloidal suspension concentrates (Col.), microgranulates, sprays and ultra-low-volume preparations (ULV) are particularly preferred.

The compositions are prepared according to methods known per se, such as by admixing the active compounds with carriers (e.g. liquid solvents, liquefied gases and/or solid carriers) optionally in the presence of surfactants (e.g. emulsifying agents and/or dispersing agents) and/or foaming agents. If water is applied as solvent, organic liquids can also be admixed with the composition as co-solvents.

As solvents or liquid carriers e.g. the following substances can be applied: aromatic compounds, such as xylene, toluene or alkylnaphthalenes, chlorinated aromatic compounds, such as chlorobenzene, chlorinated aliphatic hydrocarbons, such as methylene chloride or ethylene chloride, aliphatic hydrocarbons, such as paraffin hydrocarbons, alicyclic hydrocarbons, such as cyclohexane, alcohols, such as butyl alcohol or glycol, ethers and esters of said alcohols, ketones, such as acetone, methyl-ethyl-ketone or cyclohexanone, polar organic solvents, such as dimethyl formamide or dimethyl sulfoxide, furthermore water.

As liquified gases e.g. liquified propellants for aerosol compositions, such as halogenated hydrocarbons, furthermore liquified butane, propane, nitrogen and carbon dioxide can be applied. Of the solid carriers the following substances are to be mentioned: natural rock flours, such as kaoline, clay minerals, talc, chalk, quarz, montmorillonite or diatomaceous earth, and synthetic rock flours, such as highly disperse silicic acid, aluminium oxide and silicates. In the preparation of granular compositions first of all the following solid carriers can be applied: crushed and fractionated natural rocks, such as calcite, marble, pumice stone, sepiolite and dolomite, furthermore fluors of organic origin, such as ground tobacco stalk, ground coconut shell, etc. As emulsifying and/or foaming agents non-ionic and anionic substances, such as polyoxyethylene-fatty acid esters, polyoxyethylene-fatty alcohol ethers (e.g. alkyl-aryl-polyglycol ethers), alkylsulfates, alkylsulfonates, arylsulfonates and hydrolyzed proteins can be applied. Of the dispersing agents the following are to be mentioned: lignin, sulfite waste liquors and methyl cellulose.

The compositions may also contain stickening agents, such as carboxymethyl cellulose or powdery, granular or latex-like polymers of natural or synthetic origin (e.g. gum arabic, polyvinyl alcohol or polyvinyl acetate).

If desired, dyestuffs, such as inorganic pigments, furthermore trace elements, such as salts of boron, iron, copper, cobalt, manganese, molybdenum and zinc, can also be admixed with the active agents.

The compositions according to the invention can be applied onto the area to be treated either as such or after diluting them to the appropriate final concentration. In order to facilitate handling, transporting and storage it is preferred to prepare the compositions in the form of concentrates which can be diluted to the required final concentration directly before application.

The active agent contents of the compositions ready for use may vary within wide limits. These compositions may contain 0.01 to 95% by weight, preferably 0.01 to 10% by weight, of active agent. The compositions are applied onto the area to be treated according to known techniques, such as spraying, watering, etc.

A process for the preparation of compounds having the general formula (I), is characterized in that (a) to prepare a compound of the general formula (I) in which $R_3$ is a $C_{1-12}$ alkanoyloxy group, $R_2$ and $R_4$ each stand for hydrogen and $R_1$ and $R_5$ are as defined above, (a1) a compound of the general formula (IV),

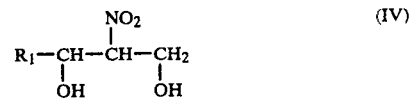

wherein $R_1$ is as defined above, is acylated; or (a2) a compound of the general formula (II),

wherein $R_1$ is as defined above, is reacted with nitroethanol in the presence of a base, and the resulting compound of the general formula (IV) is acylated; or (b) to prepare a compound of the general formula (I) in which $R_2$ and $R_4$ form together a valence bond, $R_3$ is hydrogen and $R_1$ and $R_5$ are as defined above, a compound of the general formula (II) is reacted with an organic amine or ammonium acetate, and, after removing the water formed in the reaction, the resulting Schiff-base is reacted with nitroethanol in the presence of the respective acid anhydride or carboxylic acid or with the respective nitroethanolalkanoate; or (c) to prepare a compound of the general formula (I) in which $R_3$ is hydrogen, $R_2$ and $R_4$ form together a valence bond and $R_1$ and $R_5$ are as defined above, a compound of the general formula (III),

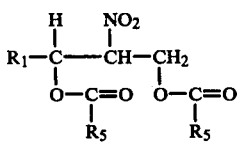

wherein $R_1$ and $R_5$ are as defined above, is heated in a solvent or is treated with a base.

According to method (a) compounds of the general formula (I), in which $R_3$ is a $C_{1-12}$ alkanoyloxy group or an optionally halogen-substituted benzoyloxy group and $R_2$ and $R_4$ each represent hydrogen, are prepared by acylating a compound of the general formula (IV). Acylation is performed in a manner known per se. The purity of the starting substance of the general formula (IV) is of particular importance, since the optional impurities affect the reaction and render the acylated end-product difficult to isolate. Acylation is performed with conventional acylating agents, preferably with acyl halides (particularly acyl chlorides) or acid anhydrides. It is preferred to perform acylation either with the respective acyl chloride at a temperature of 20° to 130° C., or with an acid anhydride at a temperature of 50° to 60° C. in the presence of a strong acid or the acyl chloride corresponding to the anhydride applied. The resulting compound of the general formula (I) can be isolated from the organic solvent after washing it with ice-cold water.

According to a preferred method of this process variant the compounds of the general formula (IV) are subjected to acylation directly in the reaction mixture where they were formed, without isolation.

The starting substances of the general formula (IV) are prepared in a manner known per se, by reacting an aldehyde of the general formula (II) with nitroethanol in the presence of a base. The reaction is performed in an organic solvent medium. It is preferred to apply an apolar solvent, an acid anhydride, chloroform or an alkanol as reaction medium. As base e.g. an inorganic base (such as an alkali metal hydroxide or carbonate) or a tertiary amine (such as triethylamine or N-methylpiperidine) can be applied. The base is applied generally in a catalytic amount. The reaction is performed preferably under cooling, at a temperature of $-5°$ C. to $+15°$ C.

According to method (b) of the invention, compounds of the general formula (I) in which $R_2$ and $R_4$ form together a valence bond and $R_3$ is hydrogen are prepared by reacting an aldehyde of the general formula (II) with an organic amine or ammonium acetate, removing the water formed in the reaction, and reacting the resulting Schiff-base either with nitroethanol in the presence of the respective acid anhydride or carboxylic acid or with the respective nitroethanolalkanoate.

It is preferred to apply, as organic amine a primary amine, particularly a lower alkylamine (such as a $C_{1-6}$ alkylamine, e.g. methylamine, ethylamine, n-butylamine, etc.) or a primary aromatic amine (such as aniline), secondary amines, such as diethylamine, can be utilized, however, as well. The reaction can be performed in an organic solvent, such as benzene, toluene, xylene, etc. The reaction is performed preferably under heating, e.g. at the boiling point of the reaction mixture.

Having removed the water formed in the reaction, the resulting Schiff-base is reacted either with nitroethanol in the presence of the respective acid anhydride or carboxylic acid, or with the respective nitroethanolalkanoate. If a compound of the general formula (I) in which $R_5$ is methyl is to be prepared, the Schiff-base is reacted either with nitroethanol in the presence of acetic anhydride or glacial acetic acid, or nitroethanol acetate is applied as reactant. The reaction is performed under heating, preferably at the boiling point of the reaction mixture. The end-product separates as a crystalline substance after cooling, admixing the reaction mixture with water or partially removing the solvent.

According to method (c) of the invention compounds of the general formula (I) in which $R_3$ is hydrogen and $R_2$ and $R_4$ form together a valence bond are prepared by heating a compound of the general formula (III) in a solvent or by treating it with a base.

Thus, according to one of the above process variants, a compound of the general formula (III) is heated in an organic solvent in the presence of an adsorbent, preferably silica gel. It is preferred to apply an aliphatic alcohol, such as methanol, ethanol, etc., as solvent. The temperature of the reaction depends on the boiling point of the reaction mixture and varies generally between about 40° and 70° C.

According to the second variant of method (c) a compound of the general formula (III) is treated with a base. As base e.g. an alkali metal carbonate (such as sodium or potassium carbonate), an alkali metal hydrocarbonate (such as sodium or potassium hydrocarbonate) or an alkali metal acetate (such as sodium or potassium acetate) can be applied. The reaction is performed preferably in a heterogeneous mixture under heating, particularly at the boiling point of the reaction mixture, or in a homogeneous mixture formed with an alcohol, without applying heating.

The pesticidal compositions according to the invention can be applied in the agriculture to advantage as spraying agents to combat the causatives of mildew infections and scabbings (Podosphaera, Uncinula, Venturia spp.) of fruit trees, diseases of tomato and potato cultures caused by Phytophthorae, Alternariae and various bacteria (such as Phytophthora infestans, Alternaria solani, Corynebacterium michigense, Xanthomonas vesicatoris) etc.

The compositions according to the invention exert particularly strong inhibiting effects on Fusarium strains, thus they can be applied to advantage in combatting the Fusarium diseases of cereals and maize either as seed dressing agents or as compositions for pre- or post-emergent treatment.

The compounds of the general formula (I) can also be applied for veterinary purposes to combat aspergillosis of useful animals, since they exert a strong inhibiting effect against Aspergillus fumigatus, the causative of this disease.

The fungicidal effects are demonstrated by the "poisoned agar" method. The compound to be tested is admixed with a solid culture medium of the fungus strain under examination, the culture medium is inoculated, and the development of the mycelia is observed. Based on the observed changes, the $EC_{50}$ values of the compounds (a concentration inhibiting the development by 50%) are determined. The results are listed in Table I, where the markings have the following meanings:

TABLE I

| Test compound (No. of example) | Fungus strain | | | | | | | |
|---|---|---|---|---|---|---|---|---|
| | Ascochyta pisi | Botrytis cinerea | Cystospora cincta | Fusarium oxysporum | Mucor globuli | Nigrospora oryzae | Phythophtora infestans | Vetricillum alboatrum |
| 1 | ++ | +++ | +++ | +++ | + | +++ | ++ | ++ |
| 6 | +++ | +++ | +++ | +++ | ++ | ++ | +++ | +++ |
| 12 | +++ | +++ | +++ | +++ | + | +++ | +++ | +++ |
| 13 | +++ | +++ | +++ | +++ | +++ | +++ | +++ | +++ |
| 15 | +++ | +++ | +++ | +++ | +++ | +++ | +++ | +++ |
| 19 | +++ | +++ | +++ | +++ | + | +++ | +++ | +++ |
| 20 | +++ | +++ | +++ | +++ | +++ | +++ | +++ | +++ |
| Dithane M-45 | − | | | − | | + | | |
| Antracol | − | | | + | | − | | |
| Ortho-Phaltan | ++ | | | + | | + | | |

Dithane-M-45: a mixture of the zinc and manganese derivatives of ethylene dithiocarbamate
Antracol: zinc compound of propylene-bis-thiocarbamate
Ortho-Phaltan: N—trichloromethyl-thio-phthalimide
+++ = $EC_{50}$ below 500 ppm
++ = $EC_{50}$ between 500 and 1000 ppm
+ = $EC_{50}$ between 1000 and 2000 ppm
− = $EC_{50}$ above 2000 ppm The inhibition of spore germination is examined so that a solution of the test compound in distilled water is admixed with the spore suspension of the fungus strain in question, next day the germinated sporae are counted under a microscope, and the percentage inhibition is calculated. The results are listed in Table II.

TABLE II

| Test compound (No. of example) | Fungus strain | Percentage inhibition Concentration (ppm) | | | | |
|---|---|---|---|---|---|---|
| | | 1 | 2 | 3 | 4 | 5 |
| 3 | Nigrospora oryzae | 4.3 | 20.9 | 51.8 | — | 100.0 |
| | Helminthosporium sativum | 22.1 | 33.3 | 36.4 | — | 100.0 |
| 6 | Nigrospora oryzae | 0.0 | 0.0 | 5.0 | — | 100.0 |
| | Helminthosporium sativum | 100.0 | 100.0 | 100.0 | 100.0 | 100.0 |
| 7 | Nigrospora oryzae | 0.0 | 16.7 | 18.0 | — | 64.8 |
| 8 | Helminthosporium sativum | 10.9 | 40.7 | 100.0 | 100.0 | 100.0 |
| 9 | Nigrospora oryzae | 20.5 | 100.0 | 100.0 | 100.0 | 100.0 |
| | Helminthosporium sativum | 100.0 | 100.0 | 100.0 | 100.0 | 100.0 |
| 11 | Nigrospora oryzae | 0.0 | — | 100.0 | — | 100.0 |
| | Helminthosporium sativum | 12.1 | — | 32.3 | — | 100.0 |
| 12 | Nigrospora oryzae | 100.0 | 100.0 | 100.0 | — | — |
| | Helminthosporium sativum | 100.0 | 100.0 | 100.0 | — | — |
| 13 | Nigrospora oryzae | 5.1 | 100.0 | 100.0 | 100.0 | 100.0 |
| | Helminthosporium sativum | 100.0 | 100.0 | 100.0 | 100.0 | 100.0 |
| 14 | Nigrospora oryzae | 0.0 | — | 100.0 | — | 100.0 |
| | Helminthosporium sativum | 2.9 | — | 86.0 | — | 100.0 |
| 15 | Nigrospora oryzae | 26.1 | 100.0 | 100.0 | — | — |
| | Helminthosporium sativum | 14.3 | 100.0 | 100.0 | — | — |
| 16 | Nigrospora oryzae | 0.0 | — | 33.5 | — | 87.1 |
| | Helminthosporium sativum | 0.0 | — | 2.3 | — | 15.3 |
| 21 | Nigrospora oryzae | 0.0 | 0.0 | 0.0 | — | 100.0 |
| 25 | Nigrospora oryzae | 38.8 | 100.0 | 100.0 | — | — |
| | Helminthosporium sativum | 47.1 | 86.9 | 100.0 | — | — |
| 34 | Helminthosporium sativum | 8.1 | 11.0 | 21.6 | — | 26.6 |
| 35 | Helminthosporium sativum | 5.5 | 10.8 | 16.4 | — | 45.2 |
| Zineb 80 WP | Nigrospora oryzae | 3.3 | — | 6.8 | — | 12.7 |
| | Helminthosporium sativum | 1.5 | 2.5 | 7.4 | 14.1 | — |

The invention is elucidated in detail by the aid of the following non-limiting examples.

EXAMPLE 1

Preparation of 1-(3,4,5-trimethoxyphenyl)-2-nitro-1,3-diacetoxy-propane 19.6 g (0.1 moles) of 3,4,5-trimethoxybenzaldehyde and 9.1 g (0.1 moles) of nitroethanol are suspended in a mixture of 25 ml of methanol and 1 ml of N-methylpiperidine at a temperature of 0° C. (under cooling with ice water). The reaction mixture is stirred for 6 hours, then 50 ml of chloroform are added, the mixture is allowed to stand at 0° C. for 72 hours and then acidified with 1 ml of acetic acid. The separated crystalline substance is filtered off, washed with chloroform and ice-cold (0° C.) water and dried. 19.7 g 68.64%) of 1-(3,4,5-trimethoxyphenyl)-2-nitro-1,3-propanediol are obtained; m.p.: 155°–159° C.

A mixture of 9.7 g (0.0337 moles) of 1-(3,4,5-trimethoxyphenyl)-2-nitro-1,3-propanediol, 13.78 g (0.135 moles) of acetic anhydride and 2.6 g of acetyl chloride is stirred at 60° C. for 4 hours. Thereafter the mixture is cooled to 20° C. and poured onto 50 g of ice. Crystallization sets in immediately. The separated product is filtered off, washed thrice with 15 ml of ice-cold water, each, and then with a small amount (about 3 ml) of isporopanol, and dried. 11.3 g (90.12%) of the title compound are obtained; m.p.: 107°–109° C.

Analysis: calculated for $C_{16}H_{21}NO_9$: C: 51.75%, H: 5.70%, N: 3.77%; found: C: 51.69%, H: 5.65%, N: 3.73%.

EXAMPLE 2

Preparation of 1-(3,4-dimethoxyphenyl)-2-nitro-1,3-diacetoxypropane 83.1 g (0.5 moles) of 3,4-dimethoxybenzaldehyde are suspended in 45.5 g (0.5 moles) of nitroethanol in the presence of 2.5 ml of triethylamine catalyst, and the mixture is stirred at 5° C. on an ice-water bath for 5.5 hours. 30 ml of chloroform are added to the reaction mixture in small portions within 5 hours. The mixture is allowed to stand for 12 hours under cooling and then acidified with 2 ml of acetic acid. The separated crystals are filtered off, washed with chloroform and ice-cold water and dried. 96.1 g (74.7%) of 1-(3,4-dimethoxyphenyl)-2-nitro-1,3-propanediol are obtained; m.p.: 134°–138° C.

A mixture of 12.85 g (0.05 moles) of 1-(3,4-dimethoxyphenyl)-2-nitro-1,3-propanediol, 20.4 g of acetic anhydride and 3.92 g of acetyl chloride is stirred at 50° C. for 5 hours. The mixture is cooled and poured onto ice. The resulting oily substance is washed twice with ice-cold water and decanted. Crystallization sets in after adding 20 ml of isopropanol to the substance. The separated crystalline product is filtered off, washed thrice with 5 ml of isopropanol and 10 ml of n-hexane, each, and dried. 11.1 g (65.1%) of the title compound are obtained; m.p.: 85°–88° C.

Analysis: calculated for $C_{15}H_{19}NO_8$: C: 52.78%, H: 5.61%, N: 4.10%; found: C: 52.72%, H: 5.58%, N: 4.12%.

EXAMPLE 3

Preparation of
1-(4-nitrophenyl)-2-nitro-1,3-diacetoxypropane 7.55 g (0.05 moles) of 4-nitrobenzaldehyde and 4.55 g (0.05 moles) of nitroethanol are suspended in a mixture of 30 ml of methanol and 0.2 ml of triethylamine. The mixture is stirred at 0° C. until dissolution (about 30 minutes) and then allowed to stand at 0° C. for 20 hours. The mixture is acidified (pH 2) with 0.2 ml of acetic acid and 0.2 ml of concentrated hydrochloric acid, and 20 ml of ice-cold water are added. The separated crystals are filtered off, washed with chloroform and dried. 8.5 g (70.24%) of 1-(4-nitrophenyl)-2-nitro-1,3-propanediol are obtained; m.p. 105°–107° C.

A mixture of 8.5 g (0.035 moles) of 1-(4-nitrophenyl)-2-nitro-1,3-propanediol, 14 g (0.13 moles) of acetic anhydride and 1 g of acetyl chloride is stirred at 60° C. for 3 hours. The mixture is cooled, poured onto 60 g of ice and stirred thoroughly. Water is decanted, 10 ml of isopropanol are added to the waxy residue, and the substance is crystallized at 0° C. The separated crystalline product is filtered off, washed with isopropanol and dried at 20° C. 8.8 g (77%) of the title compound are obtained; m.p.: 63°–66° C.

Analysis: calculated for $C_{13}H_{14}N_2O_8$: C: 47.85%, H: 4.32%, N: 8.58%; found: C: 47.74%, H: 4.19%, N: 8.62%.

EXAMPLE 4

Preparation of
1-(4-nitrophenyl)-2-nitro-1,3-dipropionylpropane 3.0 g 1-(4-nitrophenyl)-2-nitro-1,3-propanediol are suspended in 10 ml of propionic anhydride. 0.05 ml of concentrated sulfuric acid are added to the mixture, whereupon the solid dissolves immediately. The resulting solution is allowed to stand at 20° C. for 12 hours. The separated crystals are filtered off, washed with petroleum ether and recrystallized from isopropanol. 1.5 g (42.4%) of the title compound are obtained; m.p.: 61.5°–65.6° C.

Analysis: calculated for $C_{15}H_{18}N_2O_8$: C: 50.84%, H: 5.12%, N: 7.90%, O: 36.12%; found: C: 50.37%, H: 5.30%, N: 7.98%.

EXAMPLE 5

Preparation of
1-(4-acetoxy-3-methoxyphenyl)-2-nitro-1,3-diacetoxypropane 30 g (0.15 moles) of acetylvanilline are suspended in 40 ml of chloroform at −2° C., and 13.65 g (1.15 moles) of nitroethanol and 0.2 ml of triethylamine are added dropwise to the suspension at such a rate that the temperature does not rise above 10° C. The addition requires about 5 minutes. The flask is shaken during the addition, and then the reaction mixture is allowed to stand at −5° C. Crystallization sets in after about 3 hours. The mixture is allowed to stand at −5° C. for 12 hours and then it is acidified with 0.3 ml of acetic acid. The separated crystals are filtered off, washed with chloroform and dried. 14.5 g (32.8%) of the desired substance are obtained; m.p.: 89°–98° C.

12.1 g (0.04 moles) of the product obtained as described above are suspended in 24.2 ml of acetic acid at 20° C. 24.2 ml of acetyl chloride are added, whereupon the temperature of the mixture raises to 40° C. and the solid dissolves. The reaction mixture is stirred for 2 hours, then poured onto ice, stirred, and water is decanted. 10 ml of isopropanol are added to the residue, and the mixture is maintained at −5° C. for 12 hours. The separated crystals are filtered off and dried. 10.5 g (67.8%) of the title compound are obtained; m.p.: 97°–100° C. This substance is dissolved in a mixture of 80 ml of isopropanol and 10 ml of chloroform at 70° C. and recrystallized. 9.1 g (58.7%) of a pure product, melting at 103.5°–106.5° C., are obtained.

Analysis: calculated for $C_{16}H_{19}NO_9$: C: 50.42%, H: 5.36%, N: 4.00%; found: C: 52.00%, H: 4.95%, N: 3.87%.

EXAMPLE 6

Preparation of
1-cyclohexyl-2-nitro-1,3-diacetoxypropane 9.5 g (0.049 moles) of cyclohexanecarbaldehyde and 4.5 g (0.049 moles) of nitroethanol are introduced into a flask equipped with a stirrer and a thermometer. 0.3 ml of triethylamine are added, and the mixture is stirred at 0° C. for 10 hours. 15 ml of 0.5 n hydrochloric acid are introduced, the mixture is stirred for 30 minutes, thereafter 40 ml of ether are added and the mixture is stirred for additional 10 minutes. The etheral phase is separated and the aqueous phase is extracted twice with 20 ml of ether, each. The etheral phases are combined, washed with a saturated aqueous sodium chloride solution, the solvent is removed, and 15 g (0.197 moles) of acetic anhydride and 2 ml of acetyl chloride are added to the residue. The reaction mixture is stirred at 0° C., then heated to 50° C., stirred at this temperature for 2 hours and then poured onto 50 g of ice. The product is extracted from the resulting mixture with 50 ml of chloroform. The chloroform phase is washed twice with 50 ml of water, each, decolourized with activated carbon, filtered, and the solvent is removed from the filtrate. 10.5 g (77.35%) of the title compound are obtained. This substance is uniform according to thin layer chromatography; $R_f$=0.73 (adsorbent: silika gel GF 254; solvent: a 90:10:1 mixture of benzene, methanol and acetone).

Analysis: calculated for $C_{13}H_{21}NO_6$: C: 54.35%, H: 7.31%, N: 4.87%; found: C: 53.27%, H: 7.74%, N: 4.86%.

EXAMPLE 7

Preparation of 1,3-diacetoxy-2-nitro-tetradecane 4.5 g (0.024 moles) of laurylaldehyde and 4.5 g (0.049 moles) of nitroethanol are introduced into a flask equipped with a stirrer, and 0.5 ml of triethylamine are added to the mixture at 0° C. The reaction mixture is allowed to stand for 70 hours under cooling. Thereafter 15 ml of 0.5 n hydrochloric acid are introduced, and the mixture is extracted twice with 20 ml of ether, each. The etheral solution is treated with 3 drops of acetic acid, washed with saturated aqueous sodium chloride solution, and the solvent is distilled off. 18 g (0.176 moles) of acetic anhydride are added to the residue, and 2 ml of acetyl chloride are dropped into the resulting mixture. The temperature of the reaction mixture raises to 30° C. within 15 minutes. The mixture is stirred at 50° C. for 2 hours, then it is poured onto 50 g of ice, 50 ml of chloroform are added, and the resulting mixture is stirred for 10 hours. The phases are separated from each other, the aqueous phase is extracted with 50 ml of chloroform, and then the solvent is removed. 8.1 g (92.4%) of the title compound are obtained. This product is uniform according to thin layer chromatography; $R_f = 0.8$ (adsorbent: silica gel GF 254; solvent: a 60:40 mixture of toluene and ethyl acetate).

EXAMPLE 8

Preparation of 1-(4-bromophenyl)-2-nitro-1,3-diacetoxypropane

A mixture of 18.5 g (0.1 moles) of p-bromobenzaldehyde, 20 ml of methanol and 0.5 ml of triethylamine is cooled to −3° C., and 9.1 g (0.1 moles) of nitroethanol are added within one hour. The reaction mixture is stirred for 4 hours at 0°–5° C. 50 ml of water are added to the mixture, the mixture is cooled to 5° C., 30 ml of 0.5 n hydrochloric acid are added, and the mixture is stirred for 10 minutes. Thereafter 30 ml of ether are added to the mixture, the phases are separated from each other, and the etheral phase is evaporated. 30 g (0.29 moles) of acetic anhydride and 2 ml of acetyl chloride are added to the residue, the mixture is stirred at 60° C. for 2 hours, thereafter it is poured onto 100 g of ice and stirred for 3 hours. The separated product is filtered off. 28.7 g (79%) of the title compound are obtained; m.p.: 81°–82° C. According to thin layer chromatography the product is uniform; $R_f = 0.76$ (solvent: a 90:10:1 mixture of benzene, methanol and acetone).

Analysis: calculated for $C_{13}H_{14}NBrO_6$: C: 43.34%, H: 3.88%, N: 3.88%, Br: 22.20%; found: C: 43.54%, H: 4.09%, N: 3.91%, Br: 22.55%.

EXAMPLE 9

Preparation of 1-(4-methoxyphenyl)-2-nitro-3-acetoxy-propane-1

A mixture of 6.8 g (0.05 moles) of 4-methoxybenzaldehyde, 4.56 g (0.05 moles) of n-butylamine and 100 ml of benzene is refluxed under a water separating trap until the theoretical amount (0.05 moles) of water distills off. Benzene is evaporated, and 6.65 g (0.05 moles) of acetylnitroethanol, 26.0 ml of glacial acetic acid and 5.1 g (0.05 moles) of acetic anhydride are added to the residue. The reaction mixture is boiled for 0.5 hours, then cooled to 20° C., 30 ml of water are added, and crystallization is initiated by scraping. The mixture is stored in a refrigerator at 0° C. overnight in order to complete crystallization. The crystals are filtered off, washed with cold ethanol and dried. 3.0 g (26.8%) of the title compound are obtained; m.p.: 80°–82° C.

Analysis: calculated for $C_{12}H_{13}NO_5$: C: 57.37%, H: 5.21%, N: 5.58%, O: 31.84%; found: C: 57.38%, H: 5.44%, N: 5.45%, O: 31.73%.

EXAMPLE 10

Preparation of 1-(3,4,5-trimethoxyphenyl)-2-nitro-3-acetoxy-propene-1

(a) One proceeds as described in Example 9 with the difference that 19.6 g (0.1 moles) of 3,4,5-trimethoxybenzaldehyde are applied as starting substance, and 13.3 g (0.1 moles) of acetylnitroethanol, 52.0 ml of glacial acetic acid and 12.0 g (0.1 moles + excess) of a 17.6% acetic anhydride are added to the residue weighing 24.6 g. The reaction mixture is heated on a hot steam bath for one hour, then cooled to 20° C., 28 ml of water are added, and the resulting mixture is allowed to stand in a refrigerator overnight. The crystalline product is recrystallized to obtain 4.0 g (12.8%) of the title compound; m.p.: 61°–70° C.

Analysis: calculated for $C_{14}H_{17}NO_7$: C: 54.02%, H: 5.50%, N: 4.50%; found: C: 53.94%, H: 5.65%, N: 4.46%.

(b) 3.7 g (0.01 moles) of 1-(3,4,5-trimethoxyphenyl)-2-nitro-1,3-propanediol-diacetat are suspended in 30 ml of methanol, and a solution of 1 g (0.01 moles) of potassium acetate in 5 ml of methanol is added to the suspension. The reaction mixture is stirred for 5 hours on an ice-cold water bath. The separated crystalline product is filtered off, washed with water and methanol and dried. 2.8 g (90%) of the title compound are obtained; m.p.: 61°–70° C.

Analysis: calculated for $C_{14}H_{17}NO_7$: C: 54.02%, H: 5.50%, N: 4.50%; found: C: 53.54%, H: 5.65%, N: 4.46%.

EXAMPLE 11

Preparation of 1-(3,4-dimethoxyphenyl)-2-nitro-3-acetoxy-propene-1

(a) One proceeds as described in Example 9 with the difference that 15 g (0.1 moles) of 3,4-dimethoxybenzaldehyde are applied as starting substance, and 9.1 g (0.1 moles) of nitroethanol, 52 ml of glacial acetic acid and 24 g of acetic anhydride are added to the residue weighing 25.2 g. 6.4 g (22.7%) of the title compound are obtained; m.p.: 106°–108° C.

Analysis: calculated for $C_{13}H_{15}NO_6$: C: 55.51%, H: 5.38%, N: 4.98%; found: C: 55.61%, H: 5.48%, N: 4.97%.

(b) One proceeds as described in Example 10b with the difference that 3.4 g (0.01 moles) of 1-(3,4-dimethoxyphenyl)-2-nitro-1,3-diacetoxypropane are applied as starting substance. 2.6 g (92.52%) of the title compound are obtained.

Analysis: calculated for $C_{13}H_{15}NO_6$: C: 55.51%, H: 5.38%, N: 4.98%; found: C: 56.02%, H: 5.53%, N: 4.92%.

EXAMPLE 12

Preparation of 1-(3,4-methylenedioxyphenyl)-2-nitro-3-acetoxy-propene-1

One proceeds as described in Example 9 with the difference that 7.5 g (0.05 moles) of 3,4-methylenedioxybenzaldehyde are applied as starting substance. 4.6 g (34.7%) of the title compound are obtained; m.p.: 126°–128.5° C.

Analysis: calculated for $C_{12}H_{11}NO_6$: C: 54.34%, H: 4.18%, N: 5.28%; found: C: 54.36%, H: 4.26%, N: 5.36%.

EXAMPLE 13

Preparation of 1-(2-furyl)-2-nitro-3-acetoxy-propene-1

One proceeds as described in Example 9 with the difference that 13.3 g (0.1 moles) of acetylnitroethanol, 52.0 ml of glacial acetic acid and 12 g of acetic anhydride are added to the residue weighing 38.6 g. After recrystallization 6.0 g (28.7%) of the title compound are obtained; m.p.: 97°–99° C.

Analysis: calculated for $C_9H_7NO_5$: C: 51.68%, H: 3.37%, N: 6.70%; found: C: 50.76%, H: 4.35%, N: 6.65%.

EXAMPLE 14

Preparation of 1-(4-nitrophenyl)-2-nitro-3-acetoxy-propene-1

6.52 g (0.02 moles) of 1-(4-nitrophenyl)-2-nitro-1,3-propanediol-diacetate are suspended in 20 ml of methanol at 20° C. 1.3 g (0.011 moles) of powdered potassium carbonate are added, and the mixture is stirred at 20° C. until the solids dissolve. The solution is cooled gradually to 0° C. and stirred at this temperature for 10 hours. The separated crystalline product is filtered off, washed with water and methanol and dried. 4.0 g (75.2%) of the title compound are obtained; m.p.: 109°–111° C.

Analysis: calculated for $C_{11}H_{10}N_2O_6$: C: 49.63%, H: 3.86%, N: 10.52%; found: C: 49.79%, H: 3.94%, N: 10.51%.

EXAMPLE 15

Preparation of 1-phenyl-2-nitro-3-acetoxy-propene-1

(a) A 30 cm section of a glass column, 25 mm in diameter, is filled with silica gel (0.063–0.2 mm; 70–230 mesh). A solution of 5.62 g (0.02 moles) of 1-phenyl-2-nitro-1,3-propanediol-diacetate in 150 ml of methanol is passed through the column at 45° C., and then the column is washed with 100 ml of pure methanol. The methanol solutions are combined and evaporated to a final volume of about 20 ml. This residue is stored in a refrigerator for 2 hours, the separated crystalline product is filtered off, washed with a small amount of methanol and dried. 3.9 g (88.2%) of the title compound are obtained; m.p.: 80°–82° C.

(b) 5.62 g (0.02 moles) of 1-phenyl-2-nitro-1,3-propanediol-diacetate are dissolved in 25 ml of methanol at 20° C., and a solution of 2 g (0.02 moles) of potassium acetate in 7 ml of methanol is added. The resulting solution is stirred at 20° C.; crystals start to separate after about 15 minutes. The mixture is stirred in an ice-cold bath for about 3 hours, then the solids are filtered off, washed with a small amount of cold methanol and dried. 4.1 g (92.8%) of the title compound are obtained; m.p.: 80°–82° C.

Analysis: calculated for $C_{11}H_{11}NO_4$: C: 59.80%, H: 4.97%, N: 6.34%; found: C: 60.56%, H: 5.32%, N: 6.33%.

EXAMPLE 16

Preparation of 1-(3-methoxy-4-acetoxyphenyl)-2-nitro-3-acetoxy-propene-1

4.1 g (0.011 moles) of 1-(3-methoxy-4-acetoxyphenyl)-2-nitro-1,3-diacetoxypropane are dissolved in a mixture of 12 ml of acetone and 12 ml of methanol, and a solution of 0.92 g (0.011 moles) of sodium hydrocarbonate in 6 ml of water is added under stirring and ice-cooling. The reaction mixture is stirred at 0°–2° C. for 5 hours, and then the pH of the mixture is adjusted to 2–3 with 10% hydrochloric acid. The organic solution is concentrated under reduced pressure. 10 ml of ethanol are added to the residue, and the mixture is cooled to 0° C. 2.9 g (82%) of the title compound are obtained; m.p.: 82°–90° C. After recrystallization from 15 ml of acetone 2.3 g (65%) of pure product are obtained; m.p.: 101°–102° C.

Analysis: calculated for $C_{14}H_{15}NO_7$: C: 54.37%, H: 4.89%, N: 4.53%; found: C: 54.87%, H: 5.03%, N: 4.54%.

EXAMPLE 17

Preparation of 1-(4-chlorophenyl)-2-nitro-3-acetoxy-propene-1

50.55 g (0.16 moles) of 1-(4-chlorophenyl)-2-nitro-1,3-diacetoxypropane are dissolved in 300 ml of methanol, and the mixture is cooled to 0° C. 17.66 g (0.18 moles) of potassium acetate are added, and the mixture is stirred for 6 hours. The separated crystals are filtered off, washed with methanol and water, and dried. 28.8 g (70%) of the title compound are obtained; m.p.: 122°–127° C.

Analysis: calculated for $C_{11}H_{10}ClNO_4$: C: 51.68%, H: 3.94%, Cl: 13.87%, N: 5.48%; found: C: 51.66%, H: 4.56%, Cl: 13.89%, N: 5.41%.

EXAMPLE 18

Preparation of 1,3-diacetoxy-2-nitro-5,9-dimethyl-9-decene 30.8 g (0.2 moles) of 3,7-dimethyl-6-octenal are reacted with 18.2 g (0.2 moles) of nitroethanol at 0° C. for 24 hours in the presence of 0.6 ml of triethylamine catalyst. Thereafter the product is acylated and the reaction mixture is processed as described in Example 9 to obtain 30.5 g (76.74%) of the title compound as an oily substance.

Analysis: calculated for $C_{16}H_{27}NO_6$: C: 58.34%, H: 8.26%, N: 4.25%; found: C: 59.22%, H: 8.58%, N: 4.05%.

EXAMPLE 19

Preparation of 1-(3-fluorophenyl)-2-nitro-1,3-diacetoxypropane 0.5 ml of triethylamine catalyst are added to a mixture of 6.0 g (0.05 moles) of 3-fluorobenzaldehyde and 4.5 g (0.05 moles) of nitroethanol. The mixture is stirred for one hour and then allowed to stand at 0° C. for 72 hours. 15 g (0.15 moles) of acetic anhydride are added under stirring to the resulting crude 1-(3-fluorophenyl)-2-nitro-1,3-propanediol, and then 2 ml of acetyl chloride are added dropwise to the mixture. The mixture is stirred at 50° C. for 2 hours and then poured onto 100 g of ice under stirring. The resulting oily product starts to crystallize within about 15 minutes. The crude product is separated from the water, dissolved in 50 ml of chloroform, the solution is washed acid-free with ice-cold water, decolourized with activated carbon, filtered, and the solvent is evaporated under reduced pressure. 10.8 g (72%) of the title compound are obtained; m.p.: 94° C.

Analysis: calculated for $C_{13}H_{14}NFO_6$: C: 52.17%, H: 4.68%, N: 4.68%; found: C: 52.52%, H: 4.75%, N: 4.61%.

EXAMPLES 20 TO 28

The compounds listed in Table III are prepared by the methods of the previous Examples.

EXAMPLES 29 TO 43

The compounds listed in Table IV are prepared by the methods of the previous Examples.

TABLE III

| Example No. | Compound | Yield % | TLC* R_f | Running agent (TLC) on silica gel GF 254 |
|---|---|---|---|---|
| 20 | 1-(3-Cyclohexenyl)-2-nitro-1,3-diacetoxypropene | 68.3 | 0.73 | toluene-ethyl acetate 60:40 |
| 21 | 1-(4-Chlorophenyl)-2-nitro-1,3-diacetoxypropane | 82.5 | 0.7 | benzene-methanol-acetone 90:10:1 |
| 22 | 1-(2-Furyl)-2-nitro-1,3-diacetoxypropane | 61 | 0.7 | benzene-methanol-acetone 90:10:1 |
| 23 | 2-Nitro-1,3-diacetoxypentane | 51 | 0.82 | toluene-ethyl acetate 60:40 |
| 24 | 1,3-Diacetoxy-2-nitrodecane | 77.6 | 0.8 | toluene-ethyl acetate 60:40 |
| 25 | 1,3-Diacetoxy-2-nitro-4-hexene | 42 | 0.82 | toluene-ethyl acetate 60:40 |
| 26 | 1,3-Diacetoxy-2-nitro-5,9-dimethyl-9-methoxydecane | 78 | 0.83 | benzene-methanol-methyl-ethyl-ketone 60:20:20 |
| 27 | 1-(4-Methoxyphenyl)-2-nitro-1,3-diacetoxypropane | 71 | | |

*TLC = thin layer chromatography

TABLE IV

| Example No. | Compound | Yield % | Melting point °C. |
|---|---|---|---|
| 29 | 1-(3-Fluorophenyl)-2-nitro-3-acetoxy-propene-1 | 70.4 | 104.5–112 |
| 30 | 1-(3-Fluorophenyl)-2-nitro-1,3-diacetoxypropane | 10 | 106.5–114 |
| 31 | 1-Phenyl-2-nitro-1,3-di-(4-chlorobenzoyloxy)-propane | 36 | 112.5–121 |
| 32 | 1-Phenyl-2-nitro-3-lauroyloxy-propene-1 | 75 | 71.5–74 |
| 33 | 1-Phenyl-2-nitro-3-benzoyloxy-propene-1 | 73 | 86–88.5 |
| 34 | 1-Phenyl-2-nitro-1,3-di(lauroyloxy)-propane | 36 | 32–33.5 |
| 35 | 1-(3-Chlorophenyl)-2-nitro-1,3-diacetoxypropane | 78 | 88–92 |
| 36 | 1-(3-Chlorophenyl)-2-nitro-3-acetoxy-propene-1 | 69 | 84–88 |
| 37 | 1-(2-Chlorophenyl)-2-nitro-3-acetoxy-propene-1 | 65 | 40–42 |
| 38 | 1-(3,4-Methlenedioxyphenyl)-2-nitro-1,3-diacetoxypropene | 87 | 86–88.5 |
| 39 | 1-(4,6-Dichlorophenyl)-2-nitro-3-acetoxy-propene-1 | 72 | 51–62 |
| 40 | 1-(2,6-Dichlorophenyl)-2-nitro-1,3-diacetoxypropane | 63 | 83.5–88 |
| 41 | 1-(2,4-Dichlorophenyl)-2-nitro-3-acetoxy-propene-1 | 67 | 54.5–58.5 |
| 42 | 1-(3,4,5-Trimethoxyphenyl)-2-nitro-3-acetoxy-propene-1 | 73 | 90.5–103.7 |
| 43 | 1-Phenyl-2-nitro-3-propionyloxy-propene-1 | 68 | 43–45 |

EXAMPLE 44

Preparation of a wettable powder

The compound prepared as described in Example 9 or 15 is powdered in a micronizer to a particle size of 1 to 20μ. The powder is homogenized with 1 to 5% by weight of a neutral wetting agent (such as Atlox) and 20 to 60% by weight of an inert binding agent (such as kaoline or bentonite). A wettable powder is obtained.

EXAMPLE 45

Preparation of a wettable powder

One proceeds as described in Example 44 with the difference that 10 to 20% by weight of a stability-increasing acidic buffer substance (such as potassium or sodium dihydrophosphate, lactic acid, tartaric acid, etc.) are also added to the composition during the micronizing and homogenization steps. The resulting wettable powder contains about 54 to 76% by weight of active agent.

EXAMPLE 46

Preparation of a wettable powder

One proceeds as described in Example 44 or 45 with the difference that 5 to 10% by weight of a stickener, e.g. powdered whey, are also introduced.

EXAMPLE 47

Preparation of a spray composition

The compound prepared as described in Example 20 or 22 is dissolved in isopropanol to obtain a 0.1 to 1% solution. 1 to 3% of an isopropanol-soluble wetting agent (Atlox 3400B and 4851), 1% of a stickener and 1 to 5% of acetic acid are added to the solution, and the solution is filled into aerosol containers equipped with fine spray nozzles using a propellant gas (such as a freon gas, a mixture of propane and butane, carbon dioxide, etc.).

EXAMPLE 48

Preparation of an emulsifiable concentrate

The compound prepared as described in Example 20 is powdered to a particle size of 1 to 20μ, and the powdery substance is admixed with an equal weight of an inert organic solvent (e.g. xylene, petrol, rape oil, etc.) and 5 to 7% of a wetting agent. 5 to 10% of acetic acid or propionic acid can also be added to the composition in order to increase its stability.

EXAMPLE 49

Preparation of microgranules

The compound prepared as described in Example 11 is dissolved in chloroform, and the solution is applied onto a granular solid support (such as dolomite, pearlite, granular furfurol bran, coke powder, etc.) 0.8 to 1.0 mm in diameter. Microgranules containing 5 to 20% by weight of active agent are prepared.

EXAMPLE 50

Preparation of microgranules 26 parts by weight of powdered kaoline are homogenized with 15 parts by weight of starch, 1 part by weight of talc and 5 parts by weight of the compound prepared as described in Example 1, and 0.5 parts by weight of Tween 80 are added to the mixture. In the meantime 2.5 parts by weight of gelatine are swollen in 10 parts by weight of water, and further 15 parts by weight of water are added. Gelatine is dissolved in the water under heating, and the resulting solution is added to the above powder mixture. The wet mass is homogenized, passed through a 14 to 16 mesh sieve, the resulting granules are dried and then sieved again. Microgranules containing 10% by weight of active agent are obtained.

EXAMPLE 51

Preparation of a seed dressing composition

A 10% acetone solution is prepared from 6 parts by weight of the compound prepared as described in Example 15, and the solution is added to a stirred mixture of 30 parts by weight of acetone, 2.5 parts by weight of hydroxypropyl cellulose, 5 parts by weight of polyethylene glycol 6000 and 20 parts by weight of water. The resulting mixture is coloured with a dyestuff not affecting germination, and applied as seed dressing agent for the treatment of seed grains.

What we claim is:

1. A compound of the formula

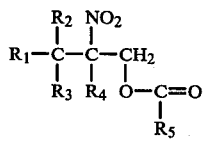

wherein $R_1$ is cyclohexyl or a phenyl group having optionally a methylenedioxy substituent, a nitro substituent or a halogen substituent, $R_2$ and $R_4$ each represent hydrogen or they form together a valence bond, $R_3$ is hydrogen or acetoxy, and $R_5$ is methyl or ethyl, with the proviso that if $R_2$ and $R_4$ each stand for hydrogen, $R_1$ is other than unsubstituted phenyl and $R_3$ may represent only acetoxy, and with the further proviso that if $R_2$ and $R_4$ form together a valence bond, and $R_5$ is methyl, $R_1$ is other than unsubstituted phenyl.

2. 1-(4-Nitrophenyl)-2-nitro-1,3-diacetoxypropane, 1-cyclohexyl-2-nitro-1,3-diacetoxypropane, 1-(4-methoxyphenyl)-2-nitro-3-acetoxy-propene-1, 1-(3,4-methylenedioxyphenyl)-2-nitro-3-acetoxy-propene-1 or 1-(3-fluorophenyl)-2-nitro-1,3-diacetoxypropane,.

3. A plant protecting composition primarily with fungicidal effects, characterized by containing as active agent one or more compound(s) of the formula

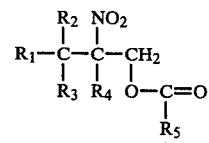

wherein $R_1$ is cyclohexyl or a phenyl group having optionally a methylenedioxy substituent, a nitro substituent or a halogen substituent, $R_2$ and $R_4$ each represent hydrogen or they form together a valence bond, $R_3$ is hydrogen or acetoxy, and $R_5$ is methyl or ethyl, with the proviso that if $R_2$ and $R_4$ each stand for hydrogen, $R_1$ is other than unsubstituted phenyl and $R_3$ may represent only acetoxy, in an amount of 0.01 to 95% by weight, together with a conventional solid or liquid carrier and optionally one or more further additive, such as a dispersing agent, a surfactant, an agent modifying the duration of the effect, a stickener and/or a stabilizer.

4. A plant protecting composition as claimed in claim 3, characterized by containing 1-phenyl-2-nitro-3-acetoxy-propene-1 as active agent.

5. A plant protecting composition as claimed in claim 3, in which said compound is 1-(4-bromophenyl)-2-nitro-1,3-diacetoxypropane.

* * * * *